US010640740B2

(12) United States Patent
Giuseppin et al.

(10) Patent No.: US 10,640,740 B2
(45) Date of Patent: May 5, 2020

(54) FERMENTATION

(71) Applicant: COOPERATIE AVEBE U.S., Veendam (NL)

(72) Inventors: Marco Luigi Federico Giuseppin, Veendam (NL); Catharina Maria Antoinette Mooij, Veendam (NL); Robin Eric Jacobus Spelbrink, Veendam (NL)

(73) Assignee: COOPERATIVE AVEBE U.A., Veendam (NL)

( * ) Notice: Subject to any disclaimer, the term of this patent is extended or adjusted under 35 U.S.C. 154(b) by 0 days.

(21) Appl. No.: 15/768,358

(22) PCT Filed: Nov. 4, 2016

(86) PCT No.: PCT/NL2016/050771
§ 371 (c)(1),
(2) Date: Apr. 13, 2018

(87) PCT Pub. No.: WO2017/078530
PCT Pub. Date: May 11, 2017

(65) Prior Publication Data
US 2018/0305646 A1 Oct. 25, 2018

(30) Foreign Application Priority Data
Nov. 6, 2015 (EP) ..................................... 15193462

(51) Int. Cl.
| | |
|---|---|
| *C12P 7/06* | (2006.01) |
| *A23C 9/12* | (2006.01) |
| *A23C 9/00* | (2006.01) |
| *C12P 7/40* | (2006.01) |
| *C12C 5/00* | (2006.01) |
| *A21D 2/08* | (2006.01) |
| *C12G 1/06* | (2019.01) |
| *C12J 1/00* | (2006.01) |
| *C12C 11/00* | (2006.01) |
| *A23L 19/20* | (2016.01) |
| *A23L 13/40* | (2016.01) |
| *A23C 13/16* | (2006.01) |
| *A23C 19/032* | (2006.01) |
| *A21D 8/04* | (2006.01) |
| *A23B 7/10* | (2006.01) |
| *C12G 1/022* | (2006.01) |
| *C12P 7/54* | (2006.01) |
| *C12P 7/56* | (2006.01) |

(52) U.S. Cl.
CPC ............... *C12C 5/004* (2013.01); *A21D 2/08* (2013.01); *A21D 8/042* (2013.01); *A21D 8/045* (2013.01); *A23B 7/105* (2013.01); *A23C 13/16* (2013.01); *A23C 19/0323* (2013.01); *A23C 19/0328* (2013.01); *A23L 13/48* (2016.08); *A23L 19/20* (2016.08); *C12C 11/003* (2013.01); *C12G 1/0203* (2013.01); *C12G 1/06* (2013.01); *C12J 1/00* (2013.01); *C12P 7/06* (2013.01); *C12P 7/54* (2013.01); *C12P 7/56* (2013.01); *A23V 2002/00* (2013.01); *A23Y 2220/17* (2013.01); *A23Y 2220/35* (2013.01); *A23Y 2220/49* (2013.01); *A23Y 2220/73* (2013.01); *A23Y 2220/77* (2013.01); *C12G 2200/15* (2013.01); *Y02E 50/17* (2013.01)

(58) Field of Classification Search
CPC ........ A23V 2300/00; A23J 1/006; C12P 7/06; C12P 7/42
IPC .................... A23C 9/12,9/00; C12P 7/40, 7/06
See application file for complete search history.

(56) References Cited

U.S. PATENT DOCUMENTS

| | | | |
|---|---|---|---|
| 2006/0204567 A1 | 9/2006 | Hu et al. | |
| 2010/0247710 A1* | 9/2010 | Giuseppin | A21D 2/264 426/20 |

FOREIGN PATENT DOCUMENTS

| | | |
|---|---|---|
| EP | 2 191 731 | 6/2010 |
| JP | H2-171182 | 7/1990 |
| JP | 2017-514527 | 6/2017 |
| WO | 2008 069 649 | 6/2008 |
| WO | 2009 061 186 | 5/2009 |

(Continued)

OTHER PUBLICATIONS

WIPO, PCT Publication No. WO 2017/078530 with International Search Report, Published Feb. 10, 2017.

(Continued)

*Primary Examiner* — Maryam Monshipouri
(74) *Attorney, Agent, or Firm* — Emerson Thomson Bennett (57) ABSTRACT

The present invention is directed to a method for decreasing the lag time in a fermentation of a culture medium to prepare a target substance, wherein the target substance is not yogurt and wherein the fermentation results in formation of acid or ethanol, which method comprises the steps of providing, to a suitable culture medium, a fermentation starter culture comprising a microorganism which liberates acid or ethanol, adding a potato protein protease inhibitor to the culture medium, culturing the microorganism, and obtaining the target substance.

It has been found that addition of potato protein protease inhibitor to a fermentation feed significantly reduces the lag time of the fermentation. The required amount of potato protein is low enough not to affect the taste of the target substance adversely, and the lag time reduction occurs both in batch- and in semi-continuous processes. The invention further pertains to a fermented food product which is not yogurt, comprising potato protein protease inhibitor.

10 Claims, 2 Drawing Sheets

(56) References Cited

FOREIGN PATENT DOCUMENTS

WO    2014 007 621    1/2014
WO    2015 112 034    7/2015

OTHER PUBLICATIONS

Ambroziak, et al., "The Use of Potato Products as Bread Quality Improvers," Research Institute of the Bakery Industry, Warsaw, Acta Alimentaria Polonica, vol. 12, No. 2, Jan. 1, 1986.
Spelbrink, R.E.J., et al., "Quantitative Determination of Trypsin Inhibitory Activity in Complex Matrices," The Open Food Science Journal, Nov. 18, 2011, vol. 5, No. 1, pp. 42-46.
Pots, et al. "The Effect of Storage of Whole Potatoes of Three Cultivars on the Patatin and Protease Inhibitor Content; a Study using Capillary Electrophoresis and MALDI-TOF Mass Spectrometry," 1999, Soc. Chem. Ind., pp. 1557-1564.
Machine translation of overview for JPH2-171182.
Machine translation of overview for 2017-514527.

\* cited by examiner

Lagtime 0,5 h    Lagtime 3,6 h

Figure 3b

Lagtime 0,6 h    Lagtime 2,2 h

FERMENTATION

The invention is in the field of fermentation. Fermentation is a well-known technique for the production of substances using the metabolic activity of microorganisms. Fermentation has been used since ancient times to increase the usable lifetime of food products. This can be achieved by selecting microorganisms that feed on such products, and that release chemical compounds that make the environment less attractive for other microorganisms. For this purpose, a fermentation feed typically comprises carbon- and nitrogen compounds as well as other nutrients sufficient for the microorganisms to live and procreate. After adding the microorganism(s) and given some time, the fermentation feed has become enriched with the compounds released by the microorganism, at which point it has become a food product, such as yogurt, cheese, wine, beer or sausage.

Microorganisms that release alcohol have been used to repel other microorganisms and retain food quality, and/or to make alcoholic drinks. Thus, plant material such as grain, rice, or berries (among which importantly grapes) has been converted by a fermentation process into for example beer, whisky, sake or wine. Various types of yeasts, such as for example yeasts from the genus *Saccharomyces* or *Candida*, are well-known for this purpose.

Also, fermentation processes have been used with the purpose of isolating the compound produced by the microorganism, rather than obtaining a food product as such. In that case, the target product is not the complete transformed fermentation feed in the form of for example beer, cheese or sausage, but the compound that is released by the microorganism. For this purpose, the compound has to be isolated from the mixture after fermentation, which further comprises the carbon- and nitrogen compounds, microorganisms and many other components. This process has been applied efficiently in the production of for instance bioethanol, where plant material is used to feed ethanol-producing microorganisms, whereupon the produced ethanol is isolated from the feed. Typical microorganisms for use in this process are yeasts from the genus such as *Saccharomyces*, but also *Zymomonas* and *Schizosaccharomyces* species are well-known for this purpose.

Microorganisms that release acid are also well-known to be used in a feed culture comprising milk, resulting in for instance cheese that has a longer shelf-life than milk. Similarly, acid-releasing microorganisms allow increasing the shelf-life of meat or vegetables by formation of for instance sausage, sauerkraut or pickles. Examples of well-known acid-releasing microorganisms for use in food production are microorganisms from the genus: *Aspergillus, Lactobacillus, Lactococcus, Streptococcus* and *Acetobacter*.

In a typical fermentation process, three phases can be distinguished. The first phase starts when the microorganisms are combined with a fermentation feed. The microorganisms adapt to their new environment, and start to take up nutrients, such as peptides, amino acids, vitamins and minerals. In this phase, the microorganisms produce enzymes required for cell division and growth, for spending energy, and for making storage materials, building blocks or nutrients, to adapt to their new environment. In this phase, however, there is barely growth, or any other visual indication that anything is happening in the fermentation. For this reason, this phase is called the lag phase.

Even though it appears nothing is happening, the lag phase is very important for the fermentation process because the microorganisms adapt to their environment, in this phase, which is important for their health. The health of the population of microorganisms determines the quality of the resulting product.

When the microorganisms have adapted to their environment, the second phase initiates. This phase, characterized by a non-substrate limited growth, is called the exponential phase. During the exponential phase, the microorganisms start to grow by cell division, and therefore multiply exponentially. In this phase, the microorganisms as a consequence of their metabolic character typically produce overflow products among which for example acids and/or alcohol.

At the end of the exponential phase, the amount of suitable nutrients has often decreased such that exponential growth can no longer be sustained by the fermenting mixture. Thus, growth slows down and the fermentation enters the stationary phase. In this phase, growth is no longer exponential, although cell division still occurs, and the fermenting mixture slowly attains an equilibrium between all present compounds. If all circumstances are appropriate, this results in a food product of high quality, with well-balanced flavor and smell, or in a mixture which is highly enriched in the compound of interest.

The time these stages require is highly variable, and dependent on the type of microorganism(s) used, the type of fermentation feed, the temperature and many other parameters. Given these distinct phases, production of target substances, among which food products (excluding yogurt) and chemical compounds such as ethanol, is commonly a batch process. As is common for batch processes, an important factor in cost is the time required for the product to be ready.

An important factor in production time is the lag phase. During this phase, the actual fermentation process is prepared. Apart from creating the adequate medium conditions for microorganism growth, there is no contribution at all to the making of the product of interest, and as such, a shorter lag time would have a huge impact on the economy of fermentation processes. However, the lag phase is very important for determining the health of the population of microorganisms, which in turn is important for the quality of the envisioned product. The time that is required for the lag phase to pass and the fermentation process to reach the exponential phase is referred to as the lag time.

Attempts to reduce the lag time have been made before. One option is to use a semi-continuous fermentation process, in which the microorganisms are adapted to the production stage and remain in the exponential phase for a prolonged time. This, however, is not suitable for many processes, because the stationary phase is important for determining the final taste and/or quality of the product, and this phase is bypassed in such a semi-continuous process.

Also, it is possible to add a mix of microorganisms, called a starter culture, which have already been adapted to the medium conditions of the fermentation. This, however, creates different problems, because in a small-scale premix microorganism feed, the environment of the full-scale fermenter is difficult to copy. It is possible to use a larger volume of the preculture (inoculum), but this has a big impact on the production process and costs of the preculture stage. Therefore, it would be preferred to reduce the lag time, possibly even further than possible with this technique, in a reliable way, with a limited amount of starter culture.

For reducing the lag time, it is also possible to add extra easily transportable and energy beneficial nutrients to the premix, as for instance extra peptides. However, this creates additional costs and problems with for instance off-taste and coloring.

SUMMARY OF THE INVENTION

The present invention is related to a method for decreasing the lag time in a fermentation of a culture medium to prepare a target substance, wherein the target substance is not yogurt and wherein the fermentation results in formation of acid or ethanol, which method comprises the steps of providing, to a suitable culture medium, a fermentation starter culture comprising a microorganism which liberates acid or ethanol, adding a potato protein protease inhibitor to the culture medium, culturing the microorganism, and obtaining the target substance. It has been found that addition of potato protein protease inhibitor to a fermentation feed significantly reduces the lag time of the fermentation. The required amount of potato protein is low enough not to affect the taste the target substance, and the lag time reduction occurs both in batch- and in semi-continuous processes. The invention further pertains to a fermented food product which is not yogurt, comprising potato protein protease inhibitor.

DETAILED DESCRIPTION

The present invention pertains to a method for decreasing the lag time in a fermentation of a culture medium to prepare a target substance, wherein the target substance is not yogurt and wherein the fermentation results in formation of acid or ethanol, which method comprises the steps of providing, to a suitable culture medium, a fermentation starter culture comprising a microorganism which liberates acid or ethanol, adding a potato protein protease inhibitor to the culture medium, culturing the microorganism, and obtaining the target substance. It has been found that addition of small amounts of potato protein protease inhibitor, such as a potato protease inhibitor isolate ("PPII"), to a fermentation feed significantly reduces the lag time of the fermentation, which has economic benefits in the production of fermentation products. The required amount of potato protein is low enough not to affect the taste of the target substance, and the lag time reduction occurs both in batch- and in semi-continuous processes. Lag time reduction, in the context of the present invention, can also be called "stimulating activity" (SA). The present invention can be applied in a wide pH- and temperature range.

The present method is directed to a method for decreasing the lag time in a fermentation of a culture medium to prepare a target substance, wherein the target substance is not yogurt. In the below, the term "food product" or "target substance" is always understood to exclude yogurt, whether or not it is explicitly mentioned.

Yogurt in this context can be defined as an acidic white, viscous but flowable dairy product obtained by fermentation of milk, such as for example cow's milk, goat's milk, sheep's milk, yak milk, mare's milk, reindeer milk, moose milk, buffalo milk, donkey milk and/or camel milk, preferably cow's milk, which has undergone fermentation using a starting culture comprising the organisms present in Kefir such as lactic acid bacteria and yeasts, as well as *Lactobacillus, Lactococcus, Bifidobacterium breve, Streptococcus thermophilus, Leuconostoc mesenteroides, Lactococcus lactis, Lactococcus cremoris*, e.g. mixtures of *Lactococcus diacetylactis* and *Leuconostoc cremoris*. In yogurt, the viscosity generally arises from the presence of exopolysaccharides, and not, as in other fermented dairy products, from precipitating protein. Culture times and conditions to obtain yogurt from milk are well-known, and depend among others on the type of microorganism used and on the type of yogurt. Other types of fermented milk products exist which are not yogurt, such as for instance cheese, sour cream, crème fraiche, quark and fermented whey.

Those components in the culture medium which the microorganisms feed on are the substrate for fermentation. This is called the fermentation feed, the fermentation broth or, as a whole, the culture medium. The culture medium generally further comprises other compounds, which may aid in the fermentation or the processing, among which salts. The culture medium is generally aqueous. The culture medium may be a food substance, in which case the substrate is comprised in the culture medium. This is the case in for instance the fermentation of food products, where the culture medium may for instance be cream or curd. Alternatively, the culture medium may be an aqueous medium to which various components have been added as substrate. Such components may include a nitrogen source, a phosphorus source and a carbon source as substrate. The nitrogen source can preferably comprise ammonia, nitrate salts, amino acids, peptides and/or protein. The carbon source is preferably a triglyceride or a carbohydrate, such as a sugar, a sugar alcohol, a starch and/or cellulose. The phosphorus source is preferably an inorganic mono-, pyro- or polyphosphate, a phosphocarbohydrate, a phospholipid or a nucleotide.

In the present invention, the target substance can be the total resulting medium after fermentation of the culture medium. This is often true for cases wherein the target substance is a food product. Alternatively, the target substance may be a component comprised in the total resulting medium after fermentation of the culture medium. In the latter case, it is preferred that the target substance is subsequently isolated from the resulting medium. This is often true in cases where the target substance is a chemical compound, such as ethanol or an acid.

That is, the present invention is directed to a method for decreasing the lag time in a fermentation of a culture medium to prepare a target substance, wherein the target substance is not yogurt and wherein the fermentation results in formation of acid or ethanol. Formation of acid or ethanol by microorganisms is known in the art, and it is well-known how to apply such formation in order to obtain a target substance by fermentation.

Preferably, the target substance is a food product, more preferably a food product produced using a fermentation which results in formation of ethanol. Alternatively, the invention is directed to fermentations which result in the formation of acid, preferably lactic acid and/or acetic acid.

In preferred embodiments, such fermentations result in food products comprising said acid. In alternative embodiments, the target substance is the acid, preferably lactic acid or acetic acid, as the target substance.

Preferably, the present invention is applied in a fermentation process in which the growth of the microorganism is peptide-limited. Peptides, for the scope of the present invention, are small protein fragments, consisting of 5-30 amino acids; such fragments are also called "nutritious peptides". Such peptides occur free in solution, so that they may also be called "free nutritious peptides".

A peptide-limited fermentation is a fermentation where the concentration of free nutritious peptides is limited but where other necessary nutrients, like (trace) minerals, carbohydrates and proteins, are freely available. Thus, a peptide-limited fermentation is a fermentation in which the quantity of free nutritious peptides present in the fermentation broth limits the growth of the microorganism. This limitation of peptides occurs when the rate of degradation of nutritious peptides by proteases/peptidases towards amino acids is higher than the rate of formation of nutritious peptides from protein. It can be tested whether a fermentation is peptide-limited by observing the effect of addition of small amounts of peptides on growth and lag time. When addition of nutritious peptides does not result in a substantially faster fermentation, then the fermentation is not peptide-limited. When addition of nutritious peptides does result in a faster fermentation, then the fermentation can be called peptide-limited.

This means that the fermentation rate is dependent on the concentration of available nutritious peptides. In case of a peptide-limited fermentation, there are insufficient nutritious peptides to sustain or to adapt towards exponential growth of the microorganism. This leads to an increase in lag time.

In the method of the present invention, addition of a relatively small amount of potato protein protease inhibitor is found to reduce the lag time, in particular for peptide-limited fermentations, and in particular where sufficient proteins are available.

It is unexpected that in particular in methods involving a peptide-limited fermentation the lag time is reduced. It is well-known that an important factor in determining the lag-time of a fermentation is the degradation of proteins in the medium to small nutritious peptides of 5-30 amino acids. This conversion is effected by a wide variety of proteases. A well-known function of protease inhibitors is to inhibit proteases, effectively inhibiting the proteases which are responsible for the degradation of proteins to nutritious peptides. As such, it would be expected that addition of protease inhibitors, of whatever source, would result in an increased lag time due to slower enzymatic degradation of proteins and an associated slower formation of nutritious peptides. However, it is now found that in fact the opposite occurs, and addition of potato protein protease inhibitors results in a reduced, rather than an increased, lag time.

The lag time, in the present context, is defined as the time duration required for the microorganism to adapt to the new environment, the culture medium. It is the time duration required for the lag phase.

A fermentation process can be monitored via various methods, using metabolic indicators or indicators in which the formation of biomass is monitored. For instance, the gas production (such as $CO_2$ or methane) might be a suitable metabolic out-put parameter in case of a fermentation which is associated with the formation of gas. Alternatively, the optical density (OD at 600 nm, OD600) might provide a suitable output parameter, to provide a quantification of the amount of microorganisms present. Also, the density of the culture medium can be suitable, in cases where a significant product of the fermentation, such as for example the target substance, has a different density than the culture medium. This is true for instance in fermentations that result in the formation of alcohol. In the case of a fermentation which results in the formation of acid, the pH may provide a suitable output parameter. The skilled person can come up with numerous ways to determine the progression of a fermentation, and determine the time required for the lag phase.

Fermentation generally progresses through an S-shaped curve in output parameters such as optical density, gas formation, density of the culture medium or pH, as is well-known in the art. In the present invention, the time to reach the half-way point in the exponential growth phase is found by calculating the inflection point in the smoothed S-curve from its second derivative. Alternatively, when using pH as an indicator of metabolic progress, take a pH-value half way the exponential curve and record the time until this pH is reached. The reduction in lag time can be determined by comparing the lag time of a fermentation without added potato protein protease inhibitor with the same fermentation wherein an appropriate quantity of potato protein protease inhibitor is added. The absolute lag time reduction is generally quantified as hours of reduction, while the relative lag time reduction is quantified as "%".

Native potato proteins can tentatively be divided into three classes (i) the patatin family, a highly homologous acidic 43 kDa glycoproteins (40-50 wt. % of the potato proteins), (ii) basic 5-25 kDa protease inhibitors (potato protein protease inhibitors), which, when isolated, are termed potato protease inhibitor isolate or "PPII"; 30-40 wt. % of the potato proteins) and (iii) other proteins mostly high molecular weight proteins (10-20 wt. % of the potato proteins) (Pots et al., *J. Sci. Food. Agric.* 1999, 79, 1557-1564).

PPII can be divided into different groups based on their molecular weight. The different groups of protease inhibitors are identified as protease inhibitor I (molecular weight of about 39 kDa), carboxypeptidase inhibitor (molecular weight of about 4 100 Da), protease inhibitors IIa and IIb (molecular weight of about 20.7 kDa), and protease inhibitor A5 (molecular weight of about 26 kDa). The ratio of these different groups of protease inhibitors in the total potato protein depends on the potato variety.

For the scope of the present invention, a potato protein protease inhibitor comprises any potato protein protease inhibitor, or any mixture of different potato proteins, which includes one or more potato protein protease inhibitors, or groups of inhibitors, as defined above. A potato protease inhibitor isolate (PPII) is an isolate comprising a potato protein protease inhibitor. A potato protein protease inhibitor according to the present invention is preferably essentially native.

PPII can be obtained in any known way, such as by e.g. precipitation, absorption, heat fractionation at 60-80° C. for at most half an hour, membrane separation, precipitation with ammonium sulphate or saturated fatty acids or other components, filtration techniques such as ultrafiltration or gel filtration. Heat fractionation results in native potato protease inhibitor isolate because the heat denatures most of the other proteins present in potato juice, but the potato protein protease inhibitors are relatively heat stable, so that they survive the heat treatment and can be isolated.

Preferably, PPII is used in the present invention. This may preferably be obtained as described in WO2008/069650, the contents of which are incorporated herein by reference, where an elaborate description of the isolation of protease inhibitors from potato fruit juice (PFJ) or potato fruit water (PFW) is described.

That process entails subjecting potato fruit juice to a flocculation by a divalent metal cation at a pH of 7-9, and centrifuging the flocculated potato fruit juice, thereby forming a supernatant. Subsequently, the supernatant is subjected to expanded bed adsorption chromatography operated at a pH of less than 11, and a temperature of 5-35° C. using an adsorbent capable of binding potato protein, thereby adsorbing the native potato protein to the adsorbent. Column materials that bind certain amounts of native potato proteins include mixed-mode adsorbentia such as for example Amersham Streamline™ Direct CST I (GE Healthcare), Fastline adsorbentia (Upfront Chromatography A/S), macroporous adsorbentia and ion exchange adsorbents. Alternatively, absorbentia comprising ligands such as disclosed in European patent application 12175944.3 are highly preferred to isolate PPII suitable for use in the present invention.

Finally, at least one native potato protein isolate is eluted from the adsorbent with an eluent. This method results among others in isolated PPII of high purity, which is native with a minimum of denatured protein present and characterized by a stable solubility.

The quantity of potato protein protease inhibitors can be determined by measuring the inhibitory against trypsin according to the method described in Spelbrink et al., The Open Food Science Journal 2011 (5) p 42-46 "Quantitative Determination Trypsin Inhibitory Activity in Complex Matrices" or in ISO 14902:2001E "Animal Feed Stuffs—Determination of soya products".

As an alternative to using potato protein protease inhibitor, such as PPII, it is possible to use a further purified protein fraction isolated from PPII. A preferred protein fraction is soluble at pH 8, has a pKa<8, has both TIA and CTIA activity, but neither activity survives heat treatment at 80° C. for 30 minutes. Nevertheless the lag time reducing capacity remains intact up to at least 90° C., and has a molecular weight between 17.5 and 18.2 kDa.

TIA activity is determined by measuring the inhibitory effect of the protein against trypsin according to the method described in Spelbrink et al, The Open Food Science Journal 2011 (5) p 42-46 "Quantitative Determination Trypsin Inhibitory Activity in Complex Matrices" or in ISO 14902:2001E "Animal Feed Stuffs—Determination of soya products".

CTIA activity is determined by measuring the inhibitory effect of the protein against chymotrypsin. The method to be used is essentially the same as the method described for TIA, but higher enzyme doses are required to compensate for chymotrypsin's lower specific activity.

An advantage of using a potato protein protease inhibitor is that the majority it is very heat stable. The active fraction in the potato protein protease inhibitor isolate that accounts for the reduction in lag time retains its native state up to temperatures of 60° C., preferably 70° C., more preferably 80° C., and most preferably 90° C. for a period of at least 15 min, preferably at least 90 min. This allows the addition of potato protein protease inhibitor at different points in the fermentation process.

Potato protein protease inhibitor can be added to the culture medium before, after or during the addition of the starter culture, or it can be added to the culture medium indirectly, e.g. by addition to the starter culture or to another component which is to be added to the culture medium. Also, it may be added to a fermentation feed which will later become or become part of the culture medium in processes wherein the fermentation feed is heated prior to fermentation. This is the case for instance in processes which require pasteurization or sterilization prior to fermentation, which is common in many processes for fermentation of food products as defined above.

It is a further advantage of the present invention that potato protein protease inhibitor is functional in fermentation processes as described in very low concentrations. In particular, addition of less than 1 g/l, preferably less than 0.5 g/l, more preferably less than 0.1 g/l, even more preferably less than 0.05 g/l of potato protein protease inhibitor is sufficient to reduce the lag time in fermentation processes according to the invention. A minimum amount of at least 0.01 g/l, preferably 0.005 g/l, more preferably 0.001 g/l potato protein protease inhibitor is required to reduce the lag time of fermentations according to the present invention.

Preferred concentrations of potato protein protease inhibitor are between for instance 5 g/l and 0.001 g/l, preferably between 5 g/l and 0.05 g/l, more preferably between 5 g/l and 0.01 g/l, such as between 1 g/l and 0.01 g/l. The concentration of potato protein protease inhibitor in this context is expressed as g potato protein protease inhibitor per liter culture medium.

At these concentrations, potato protein protease inhibitor confers no taste to the target substance, which is an additional advantage in particular when the target substance is a food product. Further additionally, these low concentrations of potato protein protease inhibitor have no detectable impact on the sensory characteristics of the target substance.

It is also an advantage of the present invention that potato protein protease inhibitor is functional in fermentation processes in a wide pH-range. In particular, the pH in the culture medium may be up to 6.7, preferably 8.0, more preferably up to 10.0. Also, the pH may be as low as 4, preferably as low as 3, more preferably as low as 2. The stability of potato protein protease inhibitor in a wide pH range is advantageous because it allows culture media of various pH's to be processed by fermentation. In addition, it allows fermentations in which acid is liberated to benefit from addition of potato protein protease inhibitor throughout the fermentation.

Furthermore, it is a distinct advantage of the present invention that potato protein protease inhibitor is non-allergenic. This means that it can be used in fermentation processes operated by people allergic to other proteins. Also, this means that it can be used in fermentation processes wherein the target substance is a food product, wherein the food product can be consumed by people with allergies without a risk of allergic shock.

In addition, it is an advantage of potato protein protease inhibitor that a solution of this protein, preferably an aqueous solution, is clear, or at least substantially non-turbid, up to concentrations of at least 10 g/L, preferably 50 g/L, more preferably 250 g/L. These concentrations are preferably attained at a solution pH of 2 to 5, preferably 2-4, more preferably 2.5-3.5. Clear or substantially non-turbid solutions of potato protein protease inhibitor allow for convenient filter sterilization and attractive appearance of the target substance, in particular when the target substance is a food product.

A fermentation starter culture, in the context of the present invention, is a culture comprising one or more microorganisms as defined above, of a composition appropriate to obtain a certain type of fermentation. A starter culture may comprise a single microorganism type, or it may comprise two or more microorganisms.

Microorganisms present in the fermentation starter culture for preparing a target substance by fermentation are those which liberate acid or ethanol. Such microorganisms are well-known. Generally, the microorganism is chosen from the group of bacteria, yeasts, fungi and algae, preferably bacteria, yeasts or fungi.

For example, suitable bacteria may be from the order of Lactobacillales, which are gram positive bacteria that comprise the lactic acid bacteria that comprises the genus *Streptococcus, Lactobacillus, Lactococcus, Carnobacterium, Leuconostoc* and *Pediococcus*, or from the order of Bifidobacteriales. However, a bacterium of the present invention is not limited to these examples.

Suitable fungi, for instance those classified as yeasts, are for example from the order of Saccharomycetales, and include species from the genera *Saccharomyces, Brettanomyces, Kloeckera* and *Candida*. However, the yeast of the present invention is not limited to these examples.

Preferred yeasts include yeasts from the genera *Saccharomyces*, such as *Saccharomyces cerevisiae*.

Other fungi include for example such as for example species from the genera *Penicillium, Mortierella, Aspergillus, Fusarium* (f.i. *Fusarium venenatum*), *Rhizopus* and *Agaricus*. However, fungi of the present invention are not limited to these examples.

Generally, suitable microorganisms for use in the method of this invention are chosen from the class of Bacilli, Actinobacteria or Saccharomycetes. Preferably, suitable microorganisms are chosen from the order of Lactobacillales, Bifidobacteriales and Saccharomycetales more preferably from the genera of *Streptococcus, Lactobacillus, Lactococcus, Bifidobacterium* and *Saccharomyces*.

*Rhizopus, Aspergillus, Mucor, Amylomyces, Endomycopsis, Saccharomyces, Hansenula anomala, Lactobacillus*, and *Acetobacter* are preferred.

The culture medium must be appropriate for the type of fermentation, the target substance and the type of microorganism concerned. Thus, the culture medium can be liquid or solid, semi-solid, particulate or viscous, and it must include suitable nutrients, among which for instance proteins and/or carbohydrates, as substrate. Suitable nutrients are well-known in the art, and can be any required component for a microorganism to grow, such as protein, peptide, lipids, trace compounds, trace elements, minerals and carbohydrates such as starch, polysaccharides and sugars.

Culturing the microorganisms is performed under suitable culture conditions. The culture conditions during fermentation can be those known for fermentation cultures suitable for the target substance of interest. Culture conditions may be aerobic or anaerobic, and if aerobic, may involve, low, regular or high aeration. Culturing can be solid state or liquid state culturing, and may be done on whatever scale, in batch or semi-continuous processing methods.

The temperature during fermentation may vary from −10° C. to +60° C., preferably from 13-45° C. Preferably, the temperature remains constant. The pH may vary from pH 2-10, preferably 4-6.7. The culturing time is highly variable and depends on the type of culture and in particular on the target substance. The skilled person is well aware of suitable culturing times for specific target substances. Accordingly, culturing times may vary from 0.5 hours to 10 years or more.

The oxygen levels may vary from absent (anaerobic fermentation) to present (aerobic fermentation). The processing may be both stirred as well as static.

Addition of the potato protein protease inhibitor may occur at any time before the fermentation. Such adding can be done by combining the potato protein protease inhibitor with the culture medium as a filtered or pasteurized protein concentrated solution, and then adding the starter culture, or alternatively, by combining the starter culture with the native potato protein and combining this mixture with the culture medium. Alternatively, all components may be added separately, or in combination with further constituents of the culture medium, as the case may be. Such further constituents of the culture medium may include for instance carbohydrates, trace minerals, bulk minerals, proteins, or peptides.

In a much preferred embodiment, the potato protein protease inhibitor can be added to the culture medium prior to a heating step. This is advantageous when the culture medium is to be heated, such as for pasteurization or sterilization, prior to addition of the starter culture. Due to the advantageous heat stability of potato protein protease inhibitor, potato protein protease inhibitor retains its native state even after such heating, so that its natural biochemical function remains and the lag time of the fermentation reduced even after heating.

Addition of potato protein protease inhibitor, preferably in native state, has the effect of reducing the lag time of the fermentation. The lag time is reduced significantly, depending on the culture and the medium, such as by at least 10%, preferably at least 25%, more preferably at least 50%, more preferably at least 60%, and most preferably at least 90%, relative to the same fermenting method wherein no potato protein protease inhibitor is added.

Obtaining (or "harvesting") the target substance may take any form known in the art for the isolation of target substances after fermentation. In particular, a whole food product may be obtained by harvesting the culture medium. Said whole food product may suitably undergo one or more after-treatments. Alternatively, a target substance may be isolated from the fermentation culture, such as by distillation, filtration, extraction or other means known in the art, and optionally further purified by any known means. This way, a target substance can be obtained with sufficient purity.

Fermentations Resulting in the Formation of Ethanol

In one embodiment of the invention, the fermentation results in formation of ethanol (alcohol). Preferably, if the method of fermentation results in formation of ethanol, the target substance is wine or sparkling wine, beer, whisky, cider, mead, sake or bioethanol. Preferred target substances are wine, beer and bioethanol, most preferably beer. In other preferred embodiments, the preferred target substance is a food product.

A preferred microorganism in this embodiment is from the genus of *Saccharomyce, Candida, Zygosaccharomyces, Dekkera* or *Brettanomyces*, preferably *Saccharomyces*. It is general knowledge what type of fermentation, using which microorganisms, results in formation of ethanol.

A preferred culture medium in this embodiment comprises plant material as substrate, such as a food-grade grain, rice, bean, honey, or fruit (preferably berry, more preferably grape), preferably grain or berry in fermentations which result in ethanol-based food products. In much preferred embodiments, the culture medium comprising plant material is a liquid medium.

Fermentation which results in formation of ethanol can generally be achieved as follows. The fermentation comprises providing a fermentation starter culture comprising one or more microorganisms from the genus of *Saccharo-*

*myce, Candida, Zygosaccharomyces, Dekkera* or *Brettanomyces* in a culture medium comprising plant material, preferably food-grade grain, rice, bean, honey, or fruit, which plant material comprises carbohydrates. The culture medium is combined with a potato protein protease inhibitor to reduce the lag time, and the microorganisms is cultured in the culture medium to obtain the food product.

Preferably in an embodiment where the fermentation is primarily directed toward producing ethanol, the fermentation is anaerobic. This is the case in for instance the fermentation of grain, rice, bean, honey, or fruit to result in beer, whisky, sake, mead, wine or bioethanol.

If the target substance is wine or sparkling wine (including champagne), suitable starter cultures comprise *Saccharomyces*. In this case, a suitable culture medium comprises berries or juice of berries, preferably grape juice or other fruit juices as substrate. The fruits can be crushed, pressed or macerated to obtain a juice to serve as a culture medium. Optionally, the juice can be treated enzymatically to increase the free sugar content or remove undesired materials.

If the target substance is beer, suitable starter cultures comprise *Saccharomyces*, such as *Saccharomyces carlsbergensis* or *Saccharomyces pastorianus*. In this case, a suitable culture medium comprises wort or other carbohydrate-rich grain extracts as substrate. The wort is prepared from grains via mashing to convert complex carbohydrates into sugars. Preferably, the grains comprise barley as a source of enzymes. Optionally, carbohydrate-converting enzymes can be added exogenously. Hops and/or other herbs and spices can be added to the wort.

If the target substance is whisky, suitable starter cultures comprise *Saccharomyces*. In this case, a suitable culture medium comprises wort or other carbohydrate-rich grain extracts as substrate. A suitable post-fermentation treatment comprises for example distillation.

If the target substance is cider, suitable starter cultures comprise *Saccharomyces*. In this case, a suitable culture medium comprises apples or apple juice as substrate.

If the target substance is mead, suitable starter cultures comprise *Saccharomyces*. In this case, a suitable culture medium comprises honey as substrate.

If the target substance is sake, suitable starter cultures comprise *Aspergillus*, preferably *Aspergillus oryzae*, and *Saccharomyces*. In this case, a suitable culture medium comprises rice as substrate.

If the target substance is bioethanol, the culture medium preferably comprises a nitrogen source, a phosphorus source and a carbon source as substrate. The nitrogen source can preferably comprise ammonia, nitrate salts, amino acids, peptides and/or protein. The carbon source is preferably a triglyceride or a carbohydrate, such as a sugar, a sugar alcohol, a starch and/or cellulose. The phosphorus source is preferably an inorganic mono-, pyro- or polyphosphate, a phosphocarbohydrate, a phospholipid or a nucleotide.

In the case of ethanol, which for example can be used as a biofuel (bioethanol), suitable microorganisms include *Saccharomyces, Zymomonas* and *Schizosaccharomyces*. The culture medium in this case preferably comprises plant material as substrate, which may be of any type, such as for example corn stalks, wheat straw, sugar cane, potato, cassava and maize.

Ethanol may be isolated from the total resulting medium after fermentation of the culture medium by distillation or reverse osmosis, membrane filtration or freeze concentration, preferably distillation. The ethanol is further preferably purified by known methods, in order to obtain ethanol as pure as possible.

Fermentations Resulting in the Formation of Acid

In another embodiment of the invention, the fermentation results in the formation of acid. Preferred acids include lactic acid and acetic acid. Preferably, if the method of fermentation results in formation of acid, the target substance is cheese, creme fraiche, sour cream, sausage, sauerkraut, pickles or vinegar. In preferred embodiments, the target substance of a fermentation which results in the formation of acid is a food product. In alternative non-food embodiments, the target substance is the acid, preferably lactic acid or acetic acid, as chemical compounds. In this embodiment, the acid is preferably isolated after the fermentation.

If the target substance is cheese, suitable starter cultures comprise various lactic acid bacteria mixtures, which are available commercially. An example is a mixture of *Lactococcus lactis* and *Lactococcus cremoris*. Other examples are bacteria of the genera *Lactobacillus, Streptococcus* or *Propionibacter*.

In this case, a suitable culture medium comprises various types of dairy products such as cream, curd or whey as substrate, such as for example dairy products derived from cow's milk, goat's milk, sheep's milk, yak milk, mare's milk, reindeer milk, moose milk, buffalo milk, donkey milk and/or camel milk, preferably cow's milk, or alternatively soybean milk and/or almond milk and/or other protein-rich plant extracts.

If the target substance is creme fraiche, the culture comprises preferably *Lactococcus* and/or *Lactobacillus*, preferably *Lactococcus lactis* subsp. *lactis, Lactococcus lactis* subsp. *cremoris*, and/or *Lactococcus lactis* biovar. *Diacetylactis*. Alternatively, cream-endogenous enzymes may be used. A suitable culture medium comprises cream, and preferably the culture medium consists of cream. Cream in this case is a dairy product as defined above, preferably derived from cow's milk.

If the target substance is sour cream, the culture comprises *Lactococcus* or *Lactobacillus* species while the culture medium comprises cream as substrate, and preferably consists of cream. Cream in this case is a dairy product as defined above, preferably derived from cow's milk.

If the target substance is sausage, suitable starter cultures comprise *Lactobacillus* (f.i. *Lb plantarum, Lb sakei, Lb farmicis, Lb curvatus*), *Micrococcus, Lactococcus, Streptococcus, Staphylococcus* (*S. xylosus* and *S. carnosus*), *Kocuria, Leuconostoc* and *Pediococcus* (f.i. *P. acidilacti* and *P. pentosaceus*) or yeasts as f.i. *Debaryomyces* spp. Mold species involved in ripening and used for inoculation include *Penicillium camembertii, P. rocquefortii* and *P. nalgiovense* and obtained from for instance Chr. Hansen (Bactoferm™). In this case, a suitable culture medium comprises (minced) meat as substrate, preferably (minced) beef, venison, horse, buffalo, pork, poultry or fish, salt and optionally sugar, GDL (Glucono-delta-Lactone), citric acid, garlic and herbs and spices.

If the target substance is sauerkraut, suitable starter cultures comprise *Leuconostoc, Lactobacillus*, and *Pediococcus*. In this case, a suitable culture medium comprises shredded cabbage, salt and optionally caraway, celery and dill seeds or other herbs and spices.

If the target substance is pickles, suitable starter cultures include *Lactobacillus* and/or *Lactococcus*. In this case, a suitable culture medium comprises vegetable chunks as well as slices, or intact vegetables. Suitable types of vegetable include cabbages, beets, cucumbers, olives and beans.

If the target substance is vinegar, suitable starter cultures comprise *Acetobacter* species. In this case, a suitable culture medium comprises wine, cider or mead.

Food Products as Target Substance

In fermentation methods according to the invention, the fermentation results in formation of acid or ethanol. In case the target substance is a food product, the culture medium preferably comprises only food-grade components. Further preferably, if the target substance is a food product, the culture medium comprises, as substrate, a nitrogen source, a phosphorus source and a carbon source, which sources are preferably provided by food-grade dairy, meat, vegetable and/or alcoholic liquid.

In case the target substance is a food product, the food product is usually obtained as the full mixture after fermentation. However, food products which are to be isolated from the fermentation mixture are not to be excluded, among which sauerkraut, pickles, vinegar, whisky, brandy, cognac and other distilled alcoholic drinks.

In case the target substance is a food product, the starter culture may comprise a single microorganism, or it may comprise two or more different microorganisms, as is known for a particular food product. The skilled person is well-aware of starter cultures comprising various microorganisms, which upon addition to a culture medium of appropriate composition results in a predetermined food product.

Optionally the food product may undergo an after-treatment after the fermentation, such as addition of additives, colorants, taste enhancers, or further ingredients, or such as additional heat treatment, such as baking, distillation, sterilization or pasteurization, or appropriate sizing, among which cutting and/or shaping, and appropriate viscosity adaption.

The invention equally pertains to a fermented food product as defined above, wherein the food product is not yogurt, comprising a potato protein protease inhibitor. Potato protein protease inhibitor in this embodiment may be native or denatured. Particularly preferred food products are wine, beer, dough, bread, cider, mead, cheese, sour cream, creme fraiche, sausage, sauerkraut or pickles, preferably wine, beer, dough, cider, mead, cheese, sour cream, creme fraiche, sausage, sauerkraut or pickles, more preferably cheese, dough, sour cream, creme fraiche, sausage or sauerkraut.

For the purpose of clarity and a concise description features are described herein as part of the same or separate embodiments, however, it will be appreciated that the scope of the invention may include embodiments having combinations of all or some of the features described.

The invention will now be illustrated by the following, non-limiting examples.

Example 1: Lag Time Reduction in a General Fermentation Model

A general fermentation model was created in which different microorganisms were tested for lag time reduction by addition of PPII. This model comprises two different media, MRS-Bouillon (MRSB, commercially available standard medium) and the so-called MRSC, which is a medium with practically the same ingredients as MRSB but instead of casein peptides, caseinate (C) is added to the medium. The peptides in MRSB generally consist of 5-30 amino acids. Depending on the microorganism needs, the MRSB medium can either be a peptide limited or a non-peptide limited system. The tested starting cultures comprised either single strain microorganism cultures (ATCC cultures) or cultures with more than one type of microorganism.

MRSB medium was prepared by dissolving the following components in 850 mL of demineralized water and adjusting the pH to 6.5. 10 g Casein peptone ("CP"), tryptic digest (Fluka 70172) 10 g Meat extract (Fluka 70164) 5 g Yeast extract (("YE", Fluka 92144) 20 g Glucose (Merck 1.08342) 1 g Tween-80 (Merck 822187) 2 g K2HPO4 (Merck 1.05104) 5 g Na-acetate (Merck 1.06267) 2 g (NH4)2 citrate (SigmaAldrich 09833) 0.2 g MgSO4-7H2O (SigmaAldrich M5921) 0.05 g MnSO4-H2O (SigmaAldrich M7634).

In MRSC medium, the casein peptone was replaced with 10 g of Caseinate (Fonterra 385). Upon dissolving the components, the total volume was brought to 1000 mL, pH was adjusted and the resulting liquid was sterilized by autoclave.

In MRSC medium, part of the (nutritious) peptides is replaced with whole protein in the form of caseinate. This is done to demonstrate that the protease inhibition activity of the PPII does not inhibit the proteases that the microorganisms need to be able to degrade the caseinate towards nutritious peptides. When the PPII would inhibit the microorganisms' proteases a prolonged lag time would be expected. The microorganisms' proteases are mostly membrane bound and the peptides made in this step are transported directly into the microorganism cell. It is therefore expected that peptidases in the medium will not have an impact as big as in the MRSB-medium. It is expected that the MRSC medium is less peptide-limited than is the MRSB medium.

For some cultures YPD medium was used as an alternative for MRSB. YPD was prepared by dissolving 20 g Casein peptone ("CP"), tryptic digest (Fluka 70172) 10 g Yeast extract (("YE", Fluka 92144) 20 g Glucose (Merck 1.08342) in a total volume of 1 L, and the resulting liquid was sterilized by autoclave.

Single strain cultures (ATCC cultures) were tested in MRSB and MRSC medium or YPD medium. See Table 1 for an overview of all tested ATCC cultures. Table 2 gives an overview of the tested cultures in MRSB, MRSC and YPD medium and the observed time reduction.

Cultures were grown from diluted stationary overnight cultures at 30° C. in a film-sealed mictrotiter plate in 100 uL of total volume that was placed in a ThermoScientific MultiSkan Go platereader while shaking periodically for 10 seconds every minute. The growth was monitored by recording the absorbance at 600 nm, and the lag time reduction was established by comparison of the growth in a culture medium with and without added potato protein protease inhibitor.

TABLE 1 various fermentation starter cultures

| Culture Description | ATCC ® code | Product |
|---|---|---|
| Lactobacillus casei | ATCC ® 334 ™ | MBL0546P |
| Lactobacillus casei | ATCC ® 393 ™ | MBL0176P |
| Lactobacillus fermentum | ATCC ® 9338 ™ | MBL0813P |
| Lactobacillus rhamnosus | ATCC ® 7469 ™ | MBL0233P |
| Lactobacillus sakei | ATCC ® 15521 ™ | MBL0128P |
| Lactococcus lactis | ATCC ® 11454 ™ | MBL0205P |
| Lactococcus lactis | ATCC ® 19435 ™ | MBL0149P |
| Acetobacter aceti | ATCC ® 15973 ™ | MBL0511P |
| Saccharomyces cerevisiae | ATCC ® 9763 ™ | MBL0699P |

All tested cultures displayed lag time reduction upon addition of PPII in MRSB or YPD medium. Optimal dosage was in most cases a final concentration of 0.50 wt. % PPII protein, but a clear effect is already shown at very low dosages of 0.05% or even at 0.01% PPII protein in the end formulation. In MRSC medium, no fermentation time elongation has been observed in these experiments. This confirms the hypothesis that PPII does not inhibit the microorganisms' proteases. In is anticipated, however, that lag-time reduction may also occur in non-peptide-limited systems. In MRSB medium all cultures showed lag time reduction upon addition of PPII.

Table 2 also shows the gained time reduction in hours (hrs.) as well as in percentages (* %).

the stimulating activity of LMW. Indeed, a stimulating effect of the addition of 0.1% LMW to the medium is observed for growth of *S. cerevisiae*, and this effect is larger in the medium with less peptides.

Figure 1:
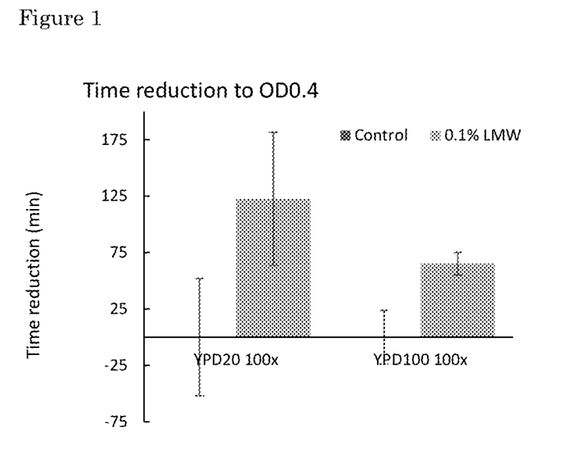
FIG. 1: Time reduction to reach OD0.4 by addition of 0.1% LMW of growth of *Saccharomyces cerevisiae* in YPD20 and YPD100. Each bar represents at least 3 different cultures. Error bars are the standard deviation.

In FIG. 1 the time reduction to reach OD 0.4, compared to cultures without LMW, is plotted. A ~2 h reduction in time (from approximately 9 h to 7 h) is seen when 0.1% LMW is added to low peptide medium, while with more peptides

TABLE 2 lag time reduction upon addition of potato protein protease inhibitor to different fermentation starter cultures.

| Culture type | Name | Medium | Acid formed | Potential products | OD600 | Time Blank (hrs:min) | Optimum PPIIconc (%) | Time PPII (hrs:min) | Time reduction hrs. (* in %) |
|---|---|---|---|---|---|---|---|---|---|
| ATCC cultures | *Lactibacillus casei* | MRSB | Lactic acid | Cheese, olives | OD600 max | 8:00 | 0.50% | 3:45 | 4:15 (*53%) |
| ATCC cultures | *Lactibacillus fermentum* | MRSB | Lactic acid | Sourdough bread | OD600 nm 0.5 | max 16:55 | 0.50% | max 8:15 | max 8:40 (*~50%) |
| ATCC cultures | *Lactibacillus rhamnosus* | MRSB | Lactic acid | Cheese | OD600 max | 2:45 | 0.50% | 0:15 | 2:30 (*91%) |
| ATCC cultures | *Lactibacillus sakei* | MRSB | Lactic acid | Meat, sausages | OD600 nm 0.5 | 19:45 | 0.50% | 0:45 | 19:00 (*96%) |
| ATCC cultures | *Lactococcus lactis* | MRSB | Lactic acid | Cheese | OD600 nm 2.00 | 19:45 | 0.05% | 7:45 | 12:00 (*61%) |
| ATCC cultures | *Acetobacter aceti* | MRSB | Acetic Acid | Vinager | Max increasing slope | 11:15 | 0.50% | 1:15 | 10:00 (*89%) |
| ATCC cultures | *Lactibacillus casei* | MRSC | Lactic acid | Cheese, olives | OD600 nm 1.00 | 17:45 | 0.50% | 6:38 | 11:07 (*62%) |
| ATCC cultures | *Lactibacillus fermentum* | MRSC | Lactic acid | Sourdough bread | OD600 nm 1.20 | 13:54 | 0.50% | 8:49 | 5:04 (*36%) |
| ATCC cultures | *Lactibacillus rhamnosus* | MRSC | Lactic acid | Cheese | OD600 nm 1.50 | 7:23 | 0.50% | 5:49 | 1:34 (*20%) |
| ATCC cultures | *Lactibacillus sakei* | MRSC | Lactic acid | Meat, sausages | NA | >19:45 | NA | >19:45 | NA |
| ATCC cultures | *Lactococcus lactis* | MRSC | Lactic acid | Cheese | OD600 nm 1.40 | 12:55 | 0.50% | 11:48 | 1:08 (*8%) |
| ATCC cultures | *Acetobacter aceti* | MRSC | Acetic acid | Vinager | Max increasing slope | 8:26 | 0.50% | 1:38 | 7:48 (*90%) |
| Comm. Baker's yeast | *Saccharomyces cerevisiae* | MRSB | Ethanol | Wine, beer | OD600 max | 4:00 | 0.50% | 2:00 | 2 (*50%) |
| | *Saccharomyces cerevisiae* | MRSC | Ethanol | Wine, beer | OD600 max | 4:00 | 0.50% | 2:00 | 2 (*50%) |

NA = not analyzable by precipitation

These data support the idea that PPII has a stimulating activity on the microbial growth, by reducing the lag time, by inhibition of peptidase activities of the microorganisms. All peptide limited systems (MRSB and YPD medium) display considerable time reduction. The richer MRSC medium showed a lower stimulating effect. All MRSB and MRSC experiments described were executed in manifold (n>4).

Example 2: Determination of Whether a Fermentation System is Peptide-Limited

The growth of *Saccharomyces cerevisiae* (ATCC 9763) was analyzed in media with two different peptide concentrations (YPD100 (containing 10 g yeast extract (YE), 20 g casein peptone (CP) and 20 g glucose per liter) and YPD20 (containing 2 g YE, 4 g CP and 20 g glucose per liter)) to see if the stimulating activity of LMW is stronger when less peptides are present. This indicates that the growth is peptide limited. Cultures were grown from diluted stationary overnight cultures at 30° C. in a film-sealed mictrotiter plate in 100 uL of total volume that was placed in a ThermoScientific MultiSkan Go platereader while shaking periodically for 10 seconds every minute. Growth was analyzed by measuring OD600, and time reduction to reach OD 0.4 is a measure of present (YPD100) the effect is smaller (approximately 1 h, from 5 to 4 hours). The time reductions measured are significant, as determined by a Student's t-test (p<0.05). In the appendix an example growth curve for each condition is shown. So LMW has a stimulating effect on the growth of *S. cerevisiae* in YPD, and the effect is strongest in peptide-limited conditions.

Example 3: Purification and Characterization of the Stimulating Agent

To find out which sub-fraction of the LMW potato protein is responsible for the lag time reduction, a potato protein concentrate was fractionated essentially according to the method of Pouvreau (L. Pouvreau, H. Gruppen, S R Piersma, L A M van den Broek, G A van Koningsveld, A G J Voragen J. Agric. Food Chem 2001, 49, p. 2864-2874 "Relative Abundance and Inhibitory Distribution of Protease Inhibitors in Potato Juice from cv. Elkana").

PPII concentrate (AVEBE) was diluted with demi water towards 1% protein solution and the pH was set to 8.0. Insolubles were removed by centrifugation at 5000 g for 10 minutes at ambient temperature. The supernatant was loaded onto a 15 by 2.6 cm column containing Source 30Q resin (GE Healthcare) and eluted using a 0 to 0.6M linear NaCl gradient. This resulted in 8 discrete protein fractions that were labeled as F1 through F8.

All fractions were tested for stimulating activity according to the method in Example 1. This revealed that fractions F1 and F6 display a strong lag time reduction, indicating that the active ingredient is in these fractions. Fractions F2, F3, F4, F7 and F8 display less lag time reduction according to these experiments and F5 shows no lag time reduction at all. Hence, the active ingredient is not present in F5. The fact that the stimulating agent binds to the column under the experimental conditions reveals that it is water-soluble at pH 8.0 and has an isoelectric point of 8.0 or lower.

Molecular weights of the fractions were determined on an Experion automated electrophoresis system (BioRad) according to the manufacturer's instructions under denaturing, reducing conditions. The fractions F1 and F6 that contain a strong stimulating activity share several MW bands, but only one of these is absent in the fraction F5 that contains no stimulating activity whatsoever: a band occurring between 17.5 and 18.2 kDa (Table 4). Hence, it follows that the presence of this band is indicative of strong stimulating activity.

TABLE 3 potato protein protease inhibitor fractionated into 8 fractions F1-F8, and the lag time reducing effect of each fraction.

| Fraction | Stimulating activity at a 0.01% dose (minutes) | Protein band present | | |
|---|---|---|---|---|
| | | 9.5 kDa | 17.5-18.2 kDa | 30 kDa |
| F1 | 60 | x | x | x |
| F2 | 5 | | | |
| F3 | 20 | | | |
| F4 | 5 | | | |
| F5 | 0 | x | | x |
| F6 | 35 | x | x | x |
| F7 | 5 | | | |
| F8 | 15 | | | |

Determination of the protease inhibitory activity was done by the method described in example 4. This revealed that protein fractions F1 and F6 contains both trypsin and chymotrypsin inhibitory activity (both TIA and CTIA), but neither activity survived a thermal treatment at 80° C. for 30 minutes.

Example 4: Potato Protein Protease Inhibitors for Use in the Present Invention can be Native A 30 g/L azocasein (SigmaAldrich, A2765) stock solution was prepared by dissolving the protein in 100 mM pH 5.0 Citrate-buffer containing 5 mM of $CaCl_2$ (SigmaAldrich, C3881) at 50° C. and cooling back to 37° C. Lyophilized fungal lysates containing protease activity were dissolved in 1 mM HCl solution. PPII was dissolved in pH 3.0 acetate solution.

From a PPII solution a series of dilutions was prepared in such a way as to cause a ~50% loss of signal upon incubation for the highest sample concentration. From each dilution, 125 µL was mixed with 25 µL of fungal protease solution in an eppendorf cup, or with 25 µL of demineralized water as a control. Positive and negative controls for the proteolytic reaction used 125 µL of demineralized water rather than sample material. To these mixtures 225 µL of warm azocasein were added, followed by a 30 minute incubation at 37.0° C. The reaction was then quenched by the addition of 150 µL of 15% w:v trichloroacetic acid ("TCA") solution. The order of addition of azocasein was the same as the order of addition of TCA to ensure equal incubation times for all samples.

Non-hydrolyzed azocasein and other insolubles were removed by centrifugation at 15,000 g at 40 C for 10 minutes in a Heraeus Multifuge 1S-R using a Thermo Scientific rotor. 100 µL of the supernatants were transferred to a microtiter plate by careful pipetting and supplemented with 100 µL of 1.5 M NaOH solution. The plate was then analyzed for absorbance at 450 nm on a BioRad Model 680 microplate reader.

Figure 2:
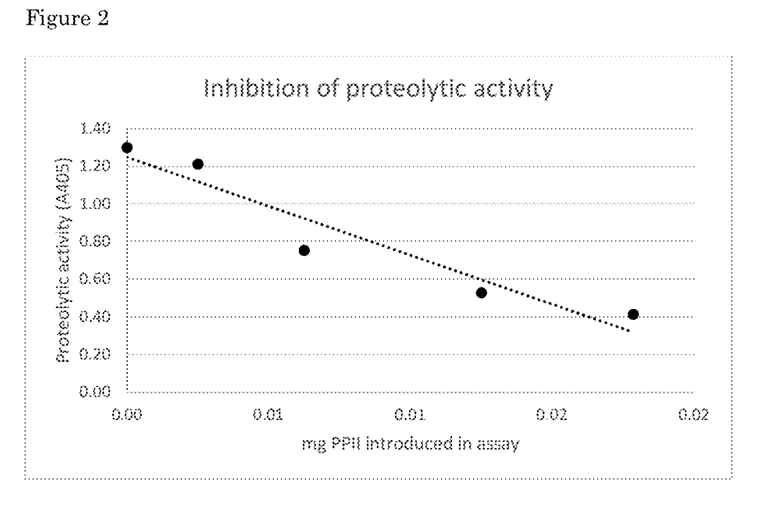
FIG. 2: Inhibition of trypsin by Solanic PPII protein.
Figure 3A:
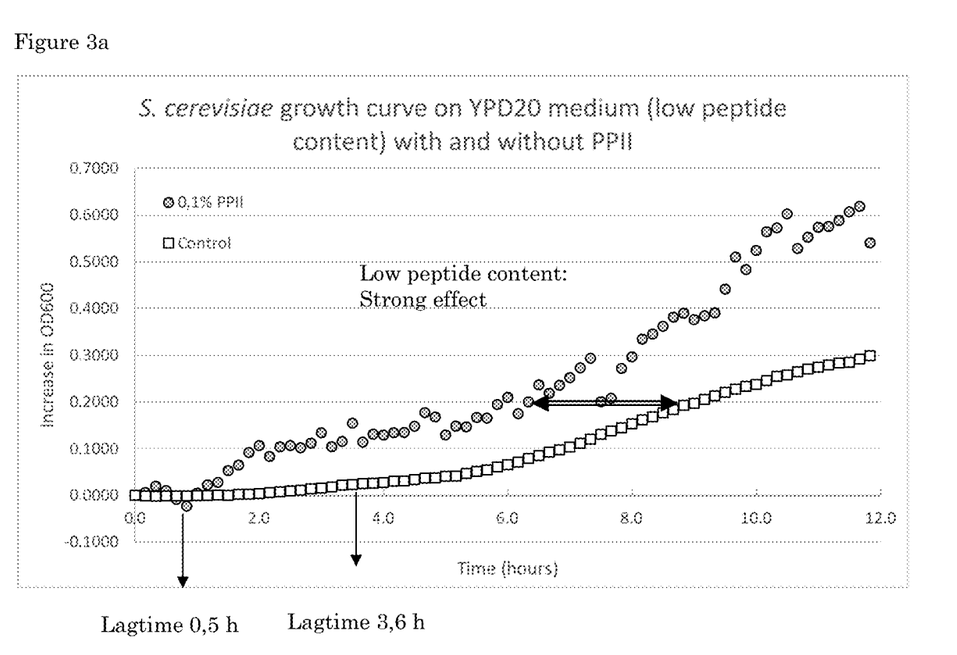
FIG. 3a&b: Example growth curves of *S. cerevisiae* with and without 0.1% potato protein protease inhibitor, showing a decreased lag time upon addition of potato protein protease inhibitor. The lag time was determined by analyzing logarithmic plots of the data. This analysis is not shown in the graph. In peptide-richer growth media, the effect is reduced.
Figure 3B:
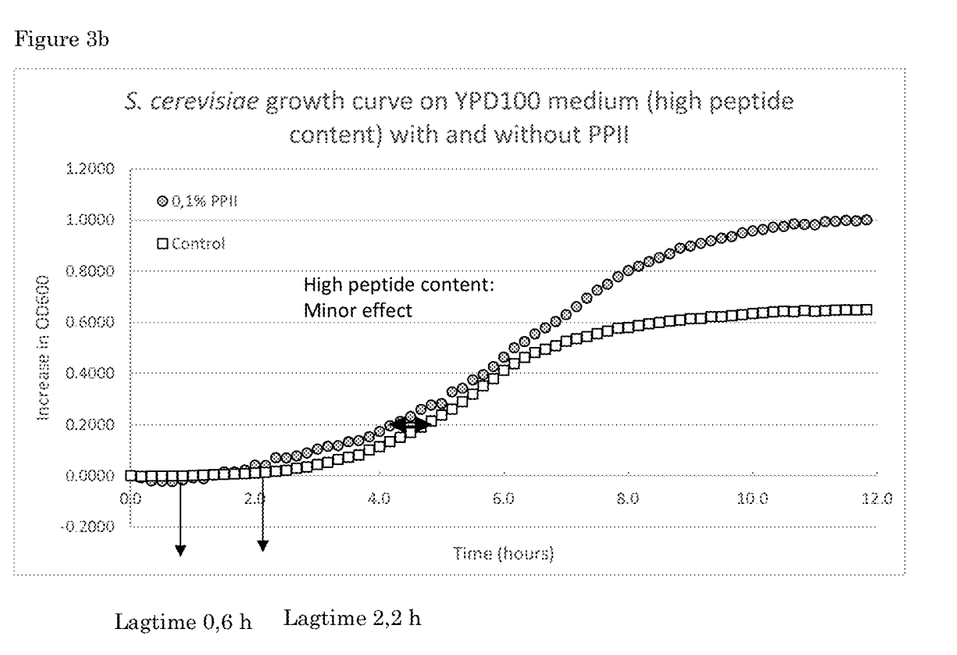

The absorbances were plotted against the amount of sample material in the plate. The slope of the resulting line was obtained via linear regression using the least squares method and indicates the amount of absorbance lost per quantity of sample material. The positive control, in the absence of sample, indicates the maximum absorbance caused by the known quantity of protease solution. Hence, by dividing the slope by the positive controls' absorbance, the trypsin inhibitory activity expressed as the amount of protease inhibited per amount of sample material was obtained (see FIG. 2).

It follows that the PPII used in the present experiments can be native.

Example 5: Malt Fermentation by *Saccharomyces cerevisiae* in the Presence of Potato Protease Inhibitors Two batches of beer were prepared from malt extract and baker yeast. An extra light colored malt extract was chosen to facilitate spectroscopic analysis. 150 g/L of Arsegan Premium Quality Malt Extract (5010012, Munton (UK)) were added to tap water and stirred until dissolved to form a wort.

10 mL of overnight culture of *Saccharomyces cerevisiae* (ATCC 9763) were added to 4 L of wort that was preheated to 30° C. The wort was split into two fractions of two liters. One was kept as a control, while the other was supplemented with 0.1 wt. % of potato protease inhibitors (Solanic 306P, Avebe). The fermentation was monitored for cell density (expressed as optical density at 620 nm), density of the liquid as measured by a hydrometer, and for the production of carbon dioxide expressed as bubbles per minute. Since the density of alcohol is less than that of water, the density of the solution is a measure of the progress of the fermentation reaction. The volume of $CO_2$ that is produced is directly related to the rate of alcohol production and therefore provides an indication of the rate of the reaction. When cell densities exceeded an OD620 of 2, aliquots were diluted with demineralized water to allow proper measurement. The reported values were corrected for this dilution.

TABLE 4

Cell densities, solution densities and $CO_2$ production rates for wort fermentation by *S. cerevisiae* in the absence and presence of 0.1 wt. % of potato protease inhibitors.

| | Reference | | | 0.1 wt % Protease Inhibitors | | |
|---|---|---|---|---|---|---|
| Time hours | Cell density OD620 | Density g/L | $CO_2$ production mL/minute | Cell density OD620 | Density g/L | $CO_2$ production mL/minute |
| 0 | 1.502 | 1054 | 0.0 | 1.561 | 1054 | 0.0 |
| 8 | 1.801 | 1052 | 0.0 | 2.060 | 1052 | 0.0 |

TABLE 4-continued

Cell densities, solution densities and $CO_2$ production rates for wort fermentation by *S. cerevisiae* in the absence and presence of 0.1 wt. % of potato protease inhibitors.

| | Reference | | | 0.1 wt % Protease Inhibitors | | |
|---|---|---|---|---|---|---|
| Time hours | Cell density OD620 | Density g/L | $CO_2$ production mL/minute | Cell density OD620 | Density g/L | $CO_2$ production mL/minute |
| 24 | 13.96 | 1034 | 1.4 | 15.51 | 1030 | 1.7 |
| 32 | 16.33 | 1022 | 0.9 | 18.04 | 1020 | 2.0 |

The presence of potato protease inhibitors resulted in higher cell densities, a more rapid decrease in solution density, and an increase in the rate of $CO_2$ production. The scent of the beer that was prepared with potato protease inhibitors was characterized by a clear fruity note, in contrast to the reference beer which lacked this attribute.

From these results, it can be seen that the overall process of fermentation is faster, which is caused by a decrease in lag time. The decrease in lag time under these conditions is approximately 2 hours.

Example 6: Sauerkraut Fermentation with Potato Protease Inhibitors

A white cabbage (purchased locally) was grated into fine slices using a kitchen food processor equipped with a grater disc. The cabbage slices thus obtained were treated with 15 grams of table salt per kg of cabbage. This treatment causes liquid to draw out of the leaves via an increase in osmotic pressure, thus forming a fermentation medium. This liquid was supplemented with an equal amount of water to facilitate pH measurement. The fermentation medium, still containing cabbage slices was split into two equal parts, were one was kept as is, while the other was supplemented with 1 g per liter of potato protease inhibitors (Solanic 206P, Avebe). The two batches were incubated side-by-side, while the pH was measured every 15 minutes by calibrated pH loggers. The time required to reach a pH of 4.0 from a starting pH of 6.0 is shown in table 5.

TABLE 5

Time required to lower the pH from 6.0 to 4.0 by endogenous microorganisms with potato protease inhibitors.

| Batch | pH | Reached after (hours:minutes) |
|---|---|---|
| Reference | 6.0 | 0:00 |
| Reference | 5.5 | 6:15 |
| Reference | 5.0 | 12:00 |
| Reference | 4.5 | 16:15 |
| Reference | 4.0 | 34:30 |
| PPI | 6.0 | 0:00 |
| PPI | 5.5 | 6:45 |
| PPI | 5.0 | 12:00 |
| PPI | 4.5 | 15:45 |
| PPI | 4.0 | 27:30 |

Sauerkraut fermentation is a complex series of reactions, in which a set of microorganisms grows out in sequence, each thereby preparing the medium for the next species. Since multiple species are involved at different times, this series is difficult to describe in terms of lag time. Nevertheless, the presence of potato protease inhibitors reduces the time required to reach a pH of 4.0 by 7 hours, or 20% of the total.

The invention claimed is:

1. A method for decreasing lag time in a fermentation of a culture medium to prepare a target substance, wherein the target substance is not yogurt, the method comprising the steps of:
   first, providing to a suitable culture medium, a fermentation starter culture comprising a microorganism which liberates acid or ethanol;
   second, adding a potato protein protease inhibitor to the culture medium,
   third, culturing the microorganism; and
   fourth, obtaining the target substance, wherein the lag time in fermentation of the culture medium is decreased in comparison to fermentation without potato protein protease inhibitor, wherein if the microorganism liberates acid, the culture medium is aqueous and/or the target substance is an acid or a food product selected from the group and consisting of cheese, crème fraîche, sour cream, sausage, sauerkraut, pickles, and vinegar, and wherein if the microorganism liberates ethanol, the culture medium is a liquid medium comprising plant material.

2. A method according to claim 1, wherein the fermentation results in formation of ethanol.

3. A method according to claim 2, wherein the fermentation starter culture comprises a microorganism from the genus of *Saccharomyces, Candida, Zygosaccharomyces, Dekkera* or *Brettanomyces*.

4. A method according to claim 2, wherein the target substance is selected from the group consisting of beer, wine, champagne, sparkling wine, cider, mead, whisky, sake, and bioethanol.

5. A method according to claim 1, wherein the fermentation results in formation of acid.

6. A method according to claim 5, wherein the fermentation starter culture comprises a microorganism from the genus of *Acetobacter, Lactococcus, Lactobacillus, Micrococcus, Streptococcus, Staphylococcus, Kocuria, Leuconostoc, Pediococcus, Debaryomyces, Penicillium* or *Leuconostoc*.

7. A method according to claim 5, wherein the target substance is lactic acid or acetic acid.

8. A method according to claim 1, wherein the quantity of free nutritious peptides limits the growth of the microorganism.

9. A method according to claim 1, wherein the concentration of potato protein protease inhibitor (grams inhibitor per liter culture medium) is between 5 g/l and 0.001 g/l.

10. A method of claim 1, wherein the target substance is an acid or a food product selected from the group consisting essentially of cheese, creème fraîche, sour cream, sausage, sauerkraut, pickles, and vinegar.

* * * * *